(12) United States Patent  
Leblanc et al.

(10) Patent No.: US 7,934,833 B2  
(45) Date of Patent: May 3, 2011

(54) IMAGE ALIGNMENT SYSTEM FOR USE IN LASER ABLATION TREATMENT OF THE CORNEA

(75) Inventors: Richard A. Leblanc, Clermont, FL (US); Hesham O. Eldeeb, Orland, FL (US)

(73) Assignee: Alcon Refractivehorizons, Inc., Forth Worth, TX (US)

( * ) Notice: Subject to any disclaimer, the term of this patent is extended or adjusted under 35 U.S.C. 154(b) by 1531 days.

(21) Appl. No.: 11/315,578

(22) Filed: Dec. 22, 2005

(65) Prior Publication Data

US 2007/0146633 A1    Jun. 28, 2007

(51) Int. Cl.  
*A61B 3/14* (2006.01)
(52) U.S. Cl. .................... 351/206; 351/205; 351/212
(58) Field of Classification Search .................. 606/4, 5, 606/10–12; 351/205–212; 607/88, 89; 128/898  
See application file for complete search history.

(56) References Cited

U.S. PATENT DOCUMENTS

| 6,547,393 | B2 * | 4/2003 | Ruiz ............................ 351/212 |
| 6,726,680 | B1 * | 4/2004 | Knopp et al. ................. 606/12 |
| 2004/0143244 | A1 | 7/2004 | Gray et al. |
| 2005/0024586 | A1 | 2/2005 | Teiwes et al. |
| 2008/0273173 | A1 * | 11/2008 | Grotehusmann et al. ...... 351/206 |
| 2010/0157244 | A1 * | 6/2010 | Leblanc ....................... 351/206 |

FOREIGN PATENT DOCUMENTS

WO    WO02087442 A1    11/2002  
WO    WO2004089214 A2    10/2004

* cited by examiner

*Primary Examiner* — Ahmed M Farah  
(74) *Attorney, Agent, or Firm* — Armando Pastrana, Jr.

(57) ABSTRACT

A system and method for aligning a first and a second image of an eye includes making a determination of a limbus location on a first eye image and a second eye image. The limbus location of the first and the second eye images are then aligned in two dimensions. A second eye feature location is determined on the first and the second eye image. One of the first and the second eye image is relatively rotated, and a correlation is performed on the first and the second eye image at a plurality of relative rotational positions using the second eye feature location. From the correlation an optimal first and second image alignment is identified.

8 Claims, 3 Drawing Sheets

IMAGE ALIGNMENT SYSTEM FOR USE IN LASER ABLATION TREATMENT OF THE CORNEA

FIELD OF THE INVENTION

The present invention is directed to laser surgery on the eye, and, more particularly, to laser ablation surgery for correcting visual impairment, and, most particularly, to systems and methods for achieving alignment between images from an analytical device and a laser surgical device.

BACKGROUND OF THE INVENTION

In custom refractive surgery on the eye, the analysis portion of the process is typically carried out prior to the surgery, for example, with a wavefront aberrometer. Subsequent to the wavefront measurement, the laser ablation portion is directed to follow a prescription generated by the analysis portion. These procedures are often separated by days.

It is desirable to align the aberrometer results with the surgical system so that the ablation is positioned properly. Aligning images of the eye with high precision is challenging. The pupil, which can be easy to find and align, varies in size over short intervals. Further, the position of the pupil within the iris changes depending upon whether it is contracting or dilating, making high-precision alignment of two eye images difficult with the use of the pupil.

The limbus remains fixed between two images, but presents a soft boundary that changes appearance with illumination. A difficult alignment component is achieving relative rotation between the two images, since the main alignment markers, the pupil and the limbus, are rotationally symmetric. It is known in the art to use artificial alignment marks placed on the eye to provide a reference. However, these marks have conflicting requirements, in that they be stable and easily seen for alignment, but easily removed after surgery. It would be highly inconvenient to retain these marks in place for the period between measurement and surgery.

Algorithms are known in the art for assisting in image alignment; however, the surgeon must confirm this alignment before proceeding with surgery. It would be beneficial to provide an image alignment process that verifies alignment and also permits adjustment of the determined alignment.

SUMMARY OF THE INVENTION

The present invention is directed to a system and method for aligning a first and a second image of an eye. The method comprises the step of determining a limbus location on a first eye image and a second eye image. The limbus location of the first and the second eye images are then aligned in two dimensions. A second eye feature is determined on the first and the second eye image. One of the first and the second eye image is relatively rotated, and a correlation is performed on the first and the second eye image at a plurality of relative rotational positions using the second eye feature. From the correlation an optimal first and second image alignment is identified.

DETAILED DESCRIPTION OF THE PREFERRED EMBODIMENTS

Figure 1:
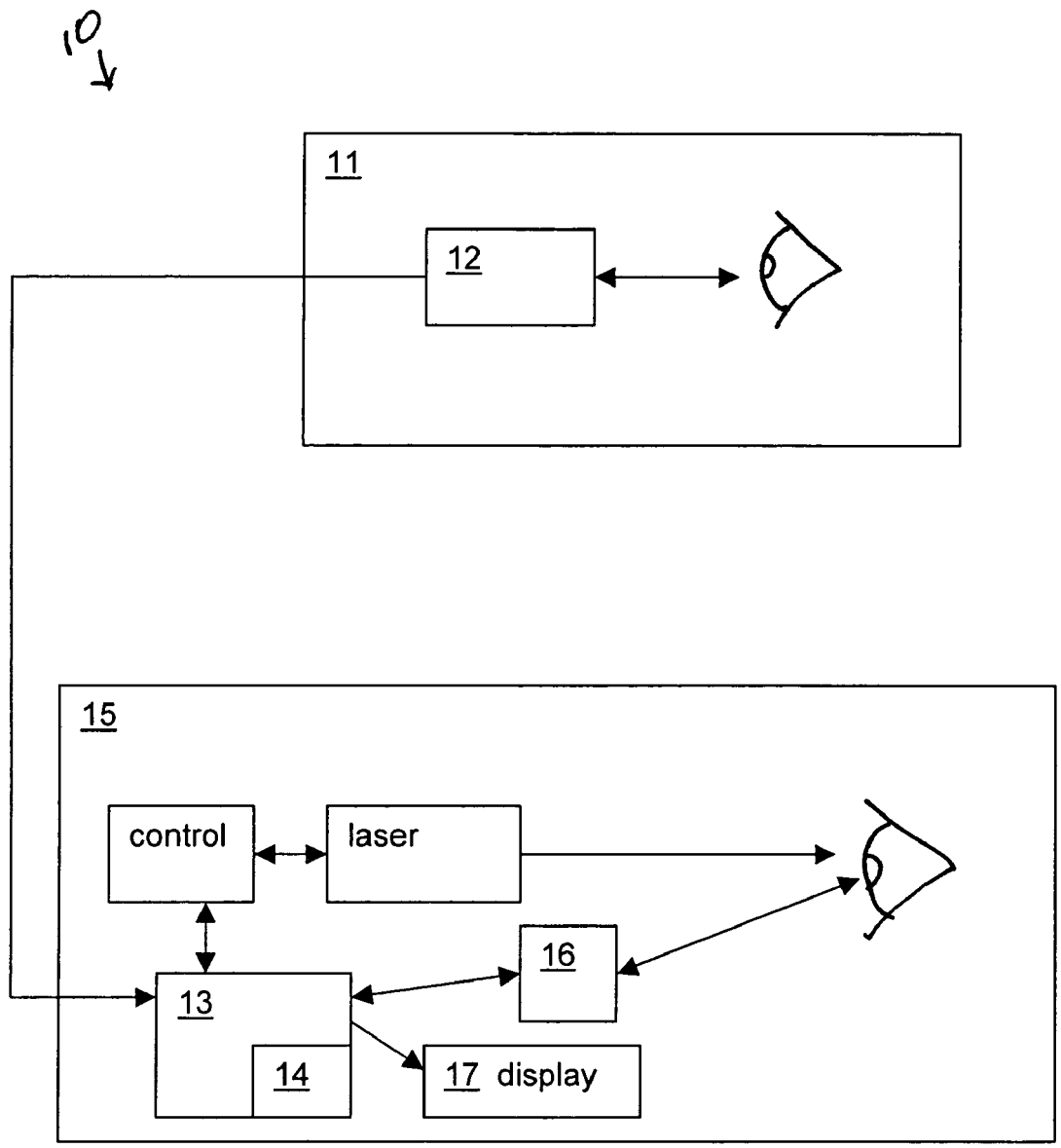
FIG. 1 is an exemplary system schematic for the present invention.
Figure 2A:
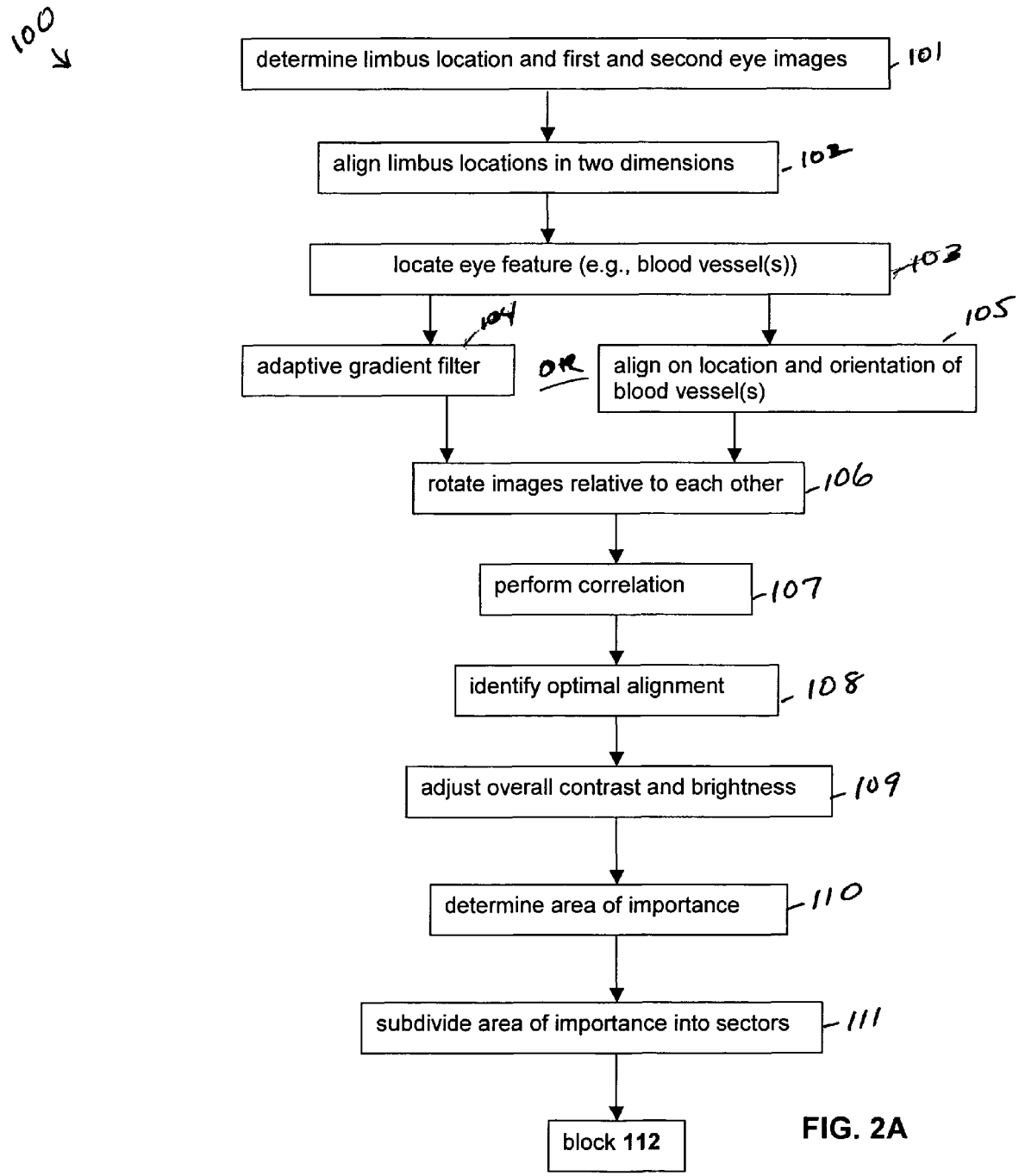
FIGS. 2A,2B is a flowchart of an exemplary embodiment of the method of the present invention.
Figure 2B:
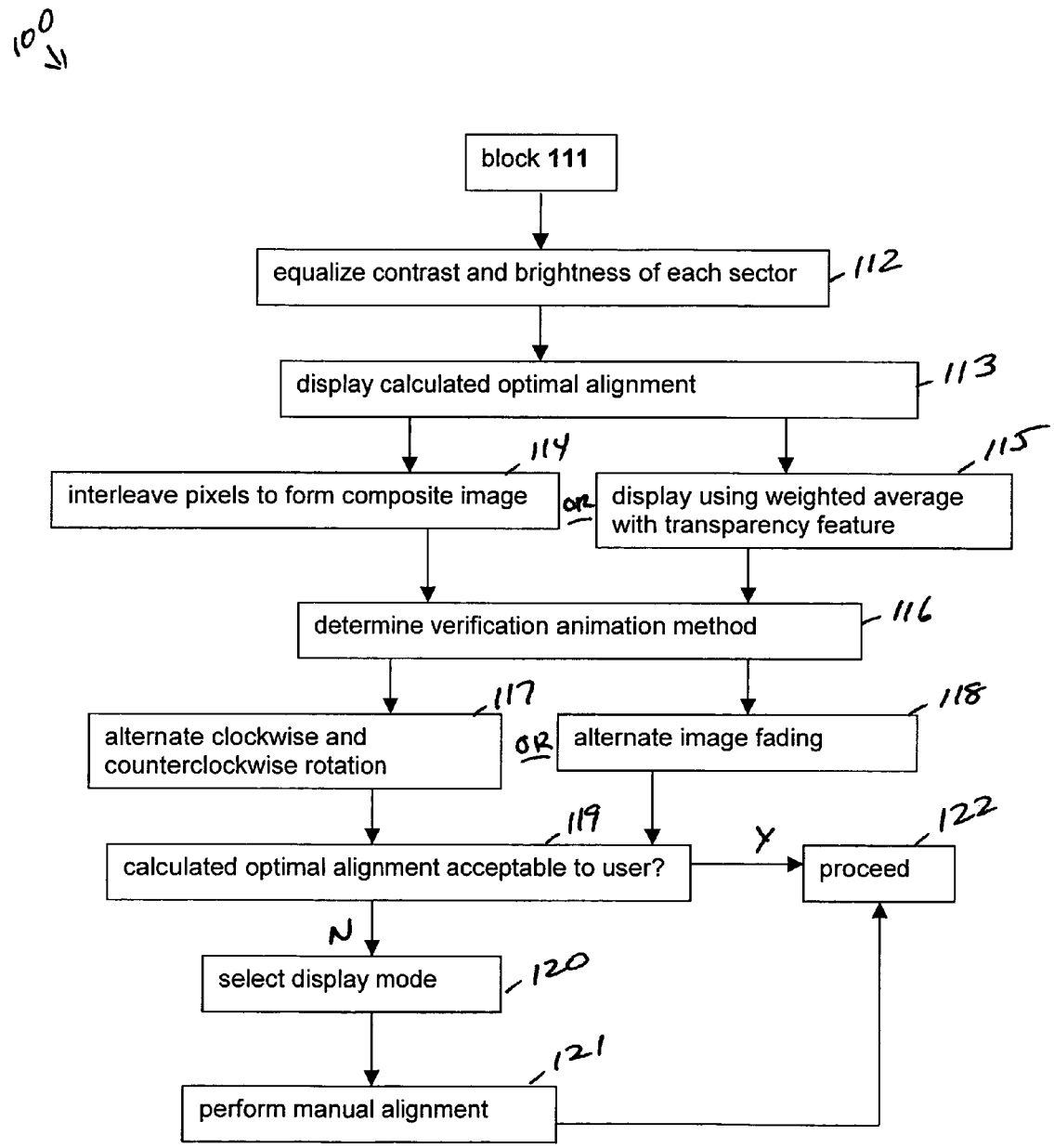

A description of preferred embodiments of the invention will now be presented with reference to FIGS. 1-2B, with an exemplary embodiment of a wavefront measurement of an eye and subsequent laser ablation surgery thereon.

A system 10 (FIG. 1) for aligning a first and a second image of an eye includes means for collecting the first and the second eye image. In a particular embodiment of laser ablation surgery, typically a first image is collected at a first location 11, for example, using a wavefront aberrometer 12. This first image is input into a processor 13 having image processing software 14 resident thereon.

When the surgery is to be conducted, a second image is collected at the surgery site 15 using a second imaging device 16. The surgeon typically wishes to view the second image during surgery on a display device 17, and would also wish to ensure that the "live" eye image is aligned with the first, previously collected, image so that the determined prescription is aligned properly with the "live" eye. Therefore, the software package 14 of the present invention is adapted to provide this alignment, and also a visual confirmation of this alignment to the surgeon.

The software package 14 includes code segments for carrying out the method 100 steps of the present invention. The method 100 (FIG. 2) includes the steps of determining a limbus location on a first eye image (block 101) and a second eye image and aligning the limbus locations in two dimensions (block 102), for example, vertically and horizontally, with reference to the calculated center of the limbus.

A second eye feature, for example, one or more blood vessels, is located on the first and the second eye images (block 103), for the purpose of providing a rotational reference point, since the limbus is substantially rotationally symmetric. Other second eye features can be used as well, such as natural eye marks and artificial eye marks. This method is believed preferable to aligning on pixel values, since the first and the second image are typically collected with different cameras under different lighting conditions. The blood vessels can be detected, for example, with the use of a gradient filter (block 104). Preferably the gradient filter is adaptive to the orientation of the blood vessel in order to maximize the accuracy of detection. If more than one blood vessel is used, each is assigned intensity values that are proportional to their prominence.

In an alternate embodiment, individual blood vessels that are common in the first and the second image are identified, and the images are aligned based upon the location and orientation of these blood vessels (block 105).

Once the limbus locations are aligned, the first and the second image are rotated relative to each other at predetermined intervals (block 106). At each point, a correlation is performed using the blood vessel location separation as an alignment criterion (block 107). From the correlation, an optimal first and second image alignment is identified (block 108).

In order that the first and the second images be properly weighted, a relative contrast and a relative brightness can be adjusted to achieve a substantial match therebetween. In particular, the first and the second image can be adjusted to have similar contrast and brightness overall (block 109). Next, an area of importance, for example, the location of the blood vessel(s) being used as reference, is determined (block 110). This area is subdivided into a plurality of sectors (block 111), and the color and brightness of each sector are equalized (block 112). The sectors may or may not be overlapping, which affects spatial filtering/smoothing. This procedure results in same details being apparent in both images.

The calculated optimal alignment is then displayed to the surgeon (block 113), preferably including the blood vessel(s). The calculation and presentation of such a display can take any of a number of forms. For example, pixels of the first and the second image can be interleaved to form a composite image; which is then displayed (block 114). The interleaving can take any of a plurality of forms, for example, alternating columns or rows, with different dimensions if desired, or pixels arranged in a "checkerboard" pattern with any size squares. Another method uses a transparency feature, wherein pixels from the first and the second image are displayed using a weighted average (block 115). In such a display, the blood vessels can be superimposed on their corresponding locations in varying levels of intensity based upon a predetermined "significance."

In order that the surgeon may verify that the calculated alignment is indeed optimal, the invention includes a feature wherein an animation is displayed of a relative rotational motion of the first and the second image about the optimal alignment. Rotation about the calculated optimal alignment is provided by means of one of a plurality of methods (block 116). In a first method, a rotation of the second image about the first is initiated to alternate between a clockwise and counter-clockwise rotation, pausing at the optimal alignment point (block 117). This method makes the image appear to "lock in" as it pauses at the midpoint of the rotation.

In a second display method, the display is faded between the two images (block 118), pausing at the points at which only one of the images is displayed. During animation, the blood vessels may also be overlaid on the images as an additional means of verification. This method imparts an apparent motion in the image if there is a misalignment, while well-aligned images have no apparent motion.

In a particular embodiment, the user is also permitted to perform a manual adjustment to the image alignment if the calculated optimal alignment is not deemed adequate (block 119). The user can choose to view the overlaid image or a dual display with the images separated but size-matched so that any change to one display is reflected in that of the other (block 120). The user can then perform adjustments, for example, by viewing or marking a common eye feature on each of the images when the images are displayed separately and then combining the images so that the marked feature can be aligned (block 121). Any number of iterations can be carried out until the user is satisfied that adequate alignment has been achieved. In an extreme case wherein adequate alignment is not achievable as determined by the user, it may be decided that a new first image is needed, in which case "proceed" (block 122) may mean returning to a first imaging device for an additional image.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the system and method illustrated and described herein are by way of example, and the scope of the invention is not limited to the exact details of construction and use.

Having now described the invention, the construction, the operation and use of preferred embodiments thereof, and the advantageous new and useful results obtained thereby, the new and useful constructions, and reasonable equivalents thereof obvious to those skilled in the art, are set forth in the appended claims.

What is claimed is:

1. A system for displaying to a user an aligned first and second image of an eye comprising:
    a first imaging device for collecting a first image of an eye;
    a second imaging device for collecting a second image of the eye;
    a processor having resident thereon a software package comprising code segments adapted for:
    determining a limbus location on the first and the second eye image;
    aligning the limbus location of the first and the second eye images in two dimensions;
    determining a location of a second eye feature on the first and the second eye image;
    relatively rotating one of the first and the second eye image;
    performing a correlation on the first and the second eye image at a plurality of relative rotational positions using the second eye feature location; and
    from the correlation, identifying an optimal first and second image alignment; and
    a display device in signal communication with the processor adapted to display to a user the optimal first and second image alignment.

2. The system recited in claim 1, wherein the second eye feature comprises at least one of a blood vessel, a natural eye mark, and an artificial eye mark.

3. The system recited in claim 1, wherein the second eye feature comprises a blood vessel, and the blood vessel location determining step comprises using a gradient filter.

4. The system recited in claim 1, wherein the first and the second image are stored as pixels, and wherein the software package further comprises code segments for interleaving pixels of the first and the second image to form a composite image, and for directing the display device to display the composite image.

5. The system recited in claim 1, wherein the software package further comprises a code segment for adjusting a relative contrast of the first and the second image to achieve a substantial match therebetween.

6. The system recited in claim 5, wherein the software package further comprises a code segment for adjusting a relative brightness of the first and the second image to achieve a substantial match therebetween.

7. The system recited in claim 1, wherein the software package further comprises code segments for calculating an animation of a relative rotational motion of the first and the second image about the optimal alignment and for directing the display device to display the calculated animation.

8. The system recited in claim 1, wherein optimal first and second image alignment display includes an image of the second eye feature in the first and the second image.

* * * * *